United States Patent [19]

Busta et al.

[11] Patent Number: 4,508,613

[45] Date of Patent: Apr. 2, 1985

[54] MINIATURIZED POTASSIUM ION SENSOR

[75] Inventors: Heinz H. Busta, Park Ridge; Kuey-Yeou Tsao, Barrington, both of Ill.; Wayne D. White, Vista, Calif.; Peter V. Loeppert, Hoffman Estates, Ill.

[73] Assignee: Gould Inc., Rolling Meadows, Ill.

[21] Appl. No.: 562,642

[22] Filed: Dec. 19, 1983

[51] Int. Cl.$^3$ ............................................. G01N 27/30
[52] U.S. Cl. .................... 204/418; 204/403; 204/416; 204/419; 204/420; 357/25
[58] Field of Search .................. 357/25; 324/71.5; 128/635; 204/416, 403, 418, 419, 420

[56] References Cited

U.S. PATENT DOCUMENTS 4,437,969  3/1984  Covington et al. ................. 204/403

OTHER PUBLICATIONS

S. M. Sze, "Physics of Semiconductor Devices", pp. 536-537, (1969).

Primary Examiner—G. L. Kaplan
Attorney, Agent, or Firm—K. H. Pierce; Edward E. Sachs

[57] ABSTRACT

A chemically sensitive device for monitoring chemical properties is described. The device includes a depletion-mode field-effect transistor. Two electrical leads are connected between source and drain region of the field-effect transistor to monitor changes in current or potential resulting from changes in the amount of chemical to be monitored. A reference electrode is attached to a lower substrate surface of the field-effect transistor and electrically connected to the source via a highly doped region adjacent to the source and another highly doped region adjacent to the reference electrode, both having a polarity identical to the substrate. A sensing membrane which is specific to the chemical to be monitored is located on a portion of the substrate remote from the gate region but electrically connected to the gate region to alter conductance between the source and the drain in accordance with the presence or absence of the chemical to be monitored. Thus, the source, gate, drain regions may be completely encapsulated to prevent contamination of the FET by the chemical to be monitored.

8 Claims, 6 Drawing Figures

MINIATURIZED POTASSIUM ION SENSOR

BACKGROUND OF THE INVENTION

A. Field of the Invention

The invention relates generally to field-effect transistors and, more specifically, to chemically sensitive field-effect transistors for monitoring chemical concentrations.

B. Description of the Prior Art

During the past decade, a general recognition that semiconductor devices may be used to enhance chemical-sensing devices has evolved. In particular, there has been a recognized need to develop enhanced means of in vivo monitoring of certain ion concentrations such as potassium in the blood. One of the earliest attempts to use a semiconductor device as an ion-sensitive device is described in U.S. Pat. No. 4,020,830 to Johnson et al. The background of the invention section of the Johnson et al. patent describes a very early attempt by Bergveld to use a metal oxide semiconductor field-effect transistor (MOSFET) which was modified by the removal of a gate metal for measuring hydrogen and sodium activities in an aqueous solution. In the Bergveld device, the MOSFET was constructed without a gate metal so that when the transistor was placed in an aqueous solution, the oxide isulation layer would become hydrated and then, with the presence of impurities in the hydrated layer, would become ion selective. After hydration of the insulation layer of the MOSFET, it was suggested that the device could be used for ion activity measurement by immersing the device in the solution in question and then recording the changes of the conductivity of the device. The Bergveld device was considered to be inaccurate by Johnson et al. and others because the output of the Bergveld device varied over the lifespan of the device.

The Johnson et al. patent sought to improve the accuracy of the device by covering the exposed gate region with a chemically-selective membrane which responded selectively to the ion to be monitored. An external reference electrode was electrically attached by a wire to the source of the field-effect transistor to provide a means of referencing the field-effect transistor to the general ionic concentration of the solution to be monitored. One problem with the device as described in the Johnson et al. patent was that exposure of the gate region of the FET to ion concentrations through the ion selective membrane produced deleterious effects on the field-effect transistor. For example, if a gate region of a field-effect transistor is exposed to a test solution, the gate insulator may become easily contaminated by the solution. Certain contaminants, such as sodium ions, have a very high mobility in silicon dioxide. Thus, the resistance and other critical properties of the gate insulator are more than likely to be altered by the exposure of the device to a solution. As a result, the response of such a device may vary greatly with time and exposure in a manner similar to the Bergveld device.

U.S. Pat. No. 4,180,771, "Chemical Sensitive Field-Effect Transistor" by Guckel, issued Dec. 25, 1979, illustrates an attempt to improve on the devices designed by Johnson and Bergveld. In the Guckel patent, a device is described in which a chemically sensitive membrane is attached to the underside of a substrate of a field-effect transistor. The chemically sensitive membrane is not directly wired to either the source, gate, or drain regions of the field-effect transistor. Instead, the chemically sensitive layer is said to provide a potential to the substrate which effects the flow of current between the source and the drain in response to the concentration of the ion to be monitored. Guckel fixes the gate voltage with a battery and allows the potential of the substrate to vary. Guckel also maintains the voltage between the source and the drain at a fixed level.

A problem encountered by all of the devices described above includes the fact that electrical connections to and from the field-effect transistors through the use of wires reduce the integrity of the devices due the possible contamination of the FET at the point of electrical contact with each wire.

SUMMARY OF THE INVENTION

A device for monitoring chemical properties is described. The device includes a semiconductor substrate formed from a material being slightly doped towards a first polarity. A biased field-effect transistor is located on the substrate. The biased field-effect transistor has doped source and drain regions that are oppositely doped with respect to the substrate. The field-effect transistor also includes a lightly doped gate region between the source and drain regions. This forms a depletion-mode device meaning that a source-to-drain current flows at zero gate voltage. The lightly doped gate region is also doped toward a polarity opposite the substrate. A reference electrode is provided which includes a reference membrane maintained by the substrate. The reference electrode provides a potential to the source through a first highly doped region near the source. The first highly doped region is doped toward the same polarity as the substrate. A chemically sensitive electrode is provided which has a chemically sensitive membrane that is supported by the substrate. The chemically sensitive membrane is located on the substrate remote from the gate region but electrically connected to the gate region by a thin-film layer of electrically conductive material. A means for monitoring the current between the source and the drain regions is provided to indicate the change in potential between the source and gate regions in response to changes in chemical concentrations as indicated by the chemically sensitive membrane electrically connected to the gate region.

DETAILED DESCRIPTION OF THE PREFERRED EMBODIMENT

The present invention is a form of a field-effect transistor (FET) which acts as an impedance transformer when monitoring certain chemical concentrations in a solution. While it is envisioned that a variety of chemical concentrations may be monitored with the present invention, the preferred embodiment is adapted to monitoring potassium concentrations in vivo. Potassium ions may vary considerably with respect to the general ion concentration in the bloodstream of a human being during certain medical emergency situations. One method of measuring potassium ion concentration is to compare the potential of a potassium-sensitive electrode relative to an electrode which is kept at a fixed potential, i.e. a reference electrode.

The general technique of using the relationship between potassium ion concentration and a fixed reference level has been used in the past to produce an output signal indicating potassium ion concentration. However, if traditional electrodes are used to produce the output signal desired, the resulting signal is relatively weak and is subject to noise. The overall system is a relatively high-impedance system and it is very difficult to produce an output signal which may be monitored. As indicated above, the present invention can be considered an impedance transformer. The present invention envisions that a signal produced in a high-impedance system such as a traditional electrode system may be changed into a strong signal in a low-impedance system and that such change can occur at the origin of the weak signal through a field-effect transistor modified in accordance with the present invention. The present invention differs from other attempts to use semiconductor devices to monitor ion concentration, in that the present invention requires only two electrical connection wires between the field-effect transistor and an external monitoring station. The present invention does not require any electrical lead wires from its sensing and reference electrodes to the field-effect transistor itself to produce a signal as previously required by the prior art systems described in the Background of the Invention section hereinabove. Furthermore, the present invention differs from previous attempts to use a field-effect transistor to monitor ion concentration in that the source, gate, and drain regions are completely encapsulated in the present invention and are not subject to contamination problems. Thus, the present invention is capable of being reproducible and capable of being a very stable monitoring device which does not degenerate significantly with respect to time.

Figure 1:
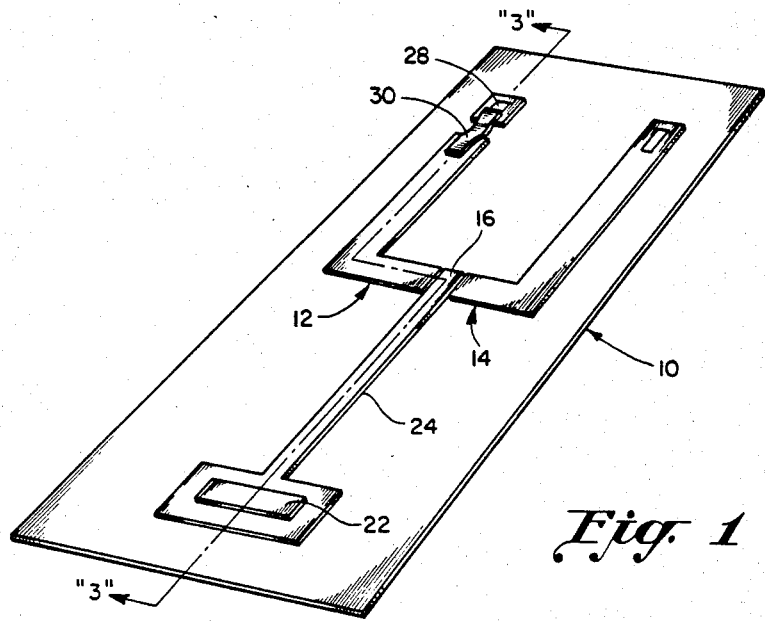
FIG. 1 is an isometric view of the present invention illustrating an isolated chemically sensitive membrane and electrical connections for the source and drain of an FET.

FIG. 1 is an isometric view of a simplified illustration of the upper side of a semiconductor device using the inventive techniques described herein. In this invention, a substrate material 10 is used to provide mechanical support. In the preferred embodiment, the substrate material 10 may be a semiconductor material which acts as the semiconductor substrate for a field-effect transistor. In other embodiments it would be adequate to have a rigid substrate material, maybe alumina or some other material that is relatively lightweight and relatively inert, with a small area of semiconductor material attached thereto to build the FET. However, in the preferred embodiment, it is much easier to build the chemical sensor of the present invention using a semiconductor substrate.

The semiconductor substrate may be either positively or negatively doped without affecting the general scope of the invention. However, for the sake of simplicity, the following discussion will assume that the substrate is a slightly-doped n-type substrate material. A source 12 and drain 14 are provided on the substrate 10. The source and drain both include regions of p-doped material in the substrate.

In the preferred embodiment, a gate region 16 between source and drain 12 and 14 is provided such that the gate region is lightly p-doped to produce a depletion-mode field-effect transistor. By providing a lightly p-doped gate region, the field-effect transistor conducts current when the gate is at zero bias so that small amounts of potential applied to the gate region will produce immediate changes in current between the source and drain of the device.

Figure 6:
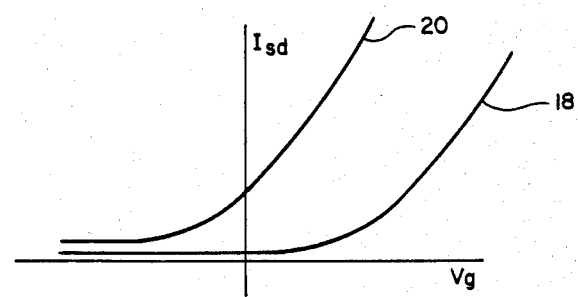
FIG. 6 is a graph of the source-to-drain current versus gate-bias characteristics for an enhancement-mode and depletion-mode FET, respectively.

FIG. 6 illustrates the difference in response of source-drain current ($I_{sd}$) versus gate voltage ($V_g$) for a conventional field-effect transistor 18 and a depletion-mode field-effect transistor 20. As can be seen, a traditional field-effect transistor will have essentially the same current output $I_{sd}$ for small changes in voltages near zero bias applied to the gate. On the other hand, incremental changes in voltage $V_g$ near zero bias for a depletion-mode field-effect transistor 20 results in a relatively large increase or decrease in the current flowing through the source-drain path. The magnitude of $I_{sd}$ at zero gate bias is, besides other factors, determined by the amount of doping in the gate region of the device. This can be easily controlled via ion implantation.

Referring again to FIG. 1, a chemically sensitive membrane 22 may be supported by substrate 10 at a location remote from gate 16 but electrically connected to the gate 16 by a thin-film connection layer 24. The chemically sensitive membrane 22 is selected from a material which has a higher sensitivity to the chemical to be monitored than other chemicals that might be present in the solution to be monitored. For example, if it is desired to monitor potassium, the chemically sensitive membrane may consist of valinomycin dissolved in an inert polymeric matrix which is above its glass transition point. Potassium ions pass more readily through the membrane whereas most other ions do not. As a consequence of the difference of the relative absorption of potassium ions on the inner and outer membrane surfaces, a potential is created across the membrane. Referring once again to FIG. 1, the potential existing at membrane 22 is transferred through conduction layer 24 to the gate region 16.

Figure 2:
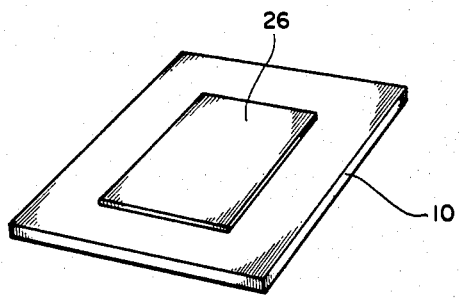
FIG. 2 is a view of the underside of a substrate for the present invention illustrating a reference membrane.

Referring now to FIG. 2, one can view the underside of the semiconductor device illustrated in FIG. 1. In FIG. 2, it is apparent that a reference membrane 26 is located on substrate 10. While in the preferred embodiment the reference membrane 26 is located on the underside of substrate 10, in other applications it may be desirable to locate reference membrane 26 elsewhere to decrease production cost. One advantage of locating reference membrane 26 on the underside of substrate 10 is that it may be easier to produce the present impedance transducer if the two sensing membranes 22 and 26 are located on opposite sides of the substrate. A unique feature of the present invention can be readily understood by viewing FIGS. 1 and 2 in combination. As can be seen from FIGS. 1 and 2, a wire lead is not necessary sary to connect the potential created at reference membrane 26 to the source 12 of the FET. Instead, a highly doped region 28 is provided on the upper portion of the substrate 10 adjacent to source region 12. The highly doped region is doped in the same polarity as the substrate. Thus, in the example provided, the highly doped region 28 is a highly n-doped region. By creating a highly n-doped region in close proximity with the source region, it is possible to transfer the potential existing at membrane 26 to a location adjacent to the source without providing a lead wire or thin-film conductive layer between the two areas. This is possible due to the fact that the highly n-doped region permits contact to the substrate thus acting as a relatively low resistive circuit. The lack of necessity to have a metallic wire or thin-film electrically conductive connection between the reference membrane located on one side of the substrate to a region adjacent to the source region on another side of the substrate greatly simplifies the manufacture of the present sensor. Furthermore, by being able to transfer the potential from the reference membrane to a region close to the source region, the present FET results in increased reliability without possible contamination of the working area of the FET. A thin-film electrically conductive layer 30 transfers the potential existing at the highly doped region 28 to the source region 12 to provide a potential to the source representing a nonselective representation of the ion level or other chemical level in a solution to be monitored. When the chemically sensitive membrane 22 indicates the presence of potassium, a potential is created at the gate region 16 causing the FET to change its current flow from source to drain.

Figure 3:
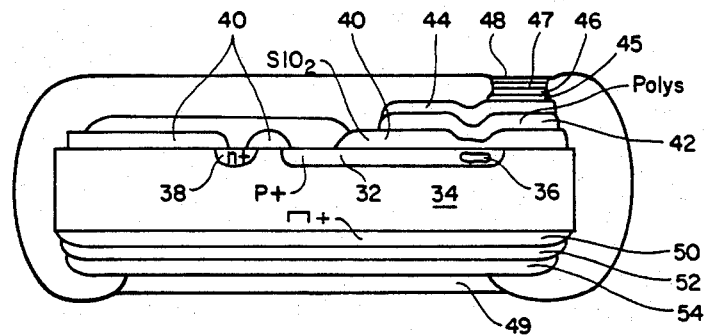
FIG. 3 is a cross-sectional view of the device illustrated in FIG. 1 taken along the line 3—3.

While FIGS. 1 and 2 illustrate the basic features of the present invention, the actual FET design may be more complex than illustrated in these two figures. For example, FIG. 3 is a cross-sectional view of a preferred embodiment of the present invention taken along the line 3—3 of FIG. 1. In FIG. 3 the source region 32 the a p+ diffusion region in the substrate 34 which is an n-doped semiconductor material. In the preferred embodiment, the gate region 36 is a lightly doped p region to cause the FET to be a depletion-mode device. A highly doped region 38 is adjacent to the source region 32. In the embodiment described, the highly doped region is an n+ region. Above the diffusion regions, and separated by an $SiO_2$ layer 40, is a discontinuous layer of polysilicon 42 to form the gate of the FET. While the polysilicon layer may not be necessary, a polysilicon/$SiO_2$ interface is well characterized and it is a very stable interface. A layer of aluminum 44 is provided over the polysilicon covering the region over the gate region 36 to provide good electrical contact to the gate. To avoid chemical attack of aluminum, a layer of silver 45 is provided on one portion of the aluminum layer between the gate region 36 and a chemically sensitive membrane 48. To form the sensing electrode, layers of silver 45, silver/silver chloride 46, and potassium chloride 47 are deposited on top of the aluminum 44. These layers are followed by an application of a chemically sensitive membrane 48. As previously discussed, if the chemical property to be determined or monitored is the level of potassium in vivo, valinomycin or any other potassium complexing chemical embedded in some carrier material such as photoresist, silicon rubber, or PVC may be used as the chemically sensitive material. The present invention envisions that other chemically sensitive membranes could be used for other applications. Other materials for ion sensing are described in Schindler, J. G. and Gulich, M. V. "Technology of Electrochemical Solid-Contact Catheter Sensors and Telescope Catheter Electrode Systems for the Measurement of $Ca^{++}$, $K^+$, $Na^+$, $Cl^-$, Urea, pH, $O_2$ and $CO_2$." Biomed. Technik 26 (1981), 43–53 which is incorporated herein by reference.

In the preferred embodiment, the reference electrode 49 is placed on the underside, or opposite side, of the substrate 34. By placing the reference electrode on the opposite side from the chemically selective membrane 48, it is possible to obtain enhanced isolation of the working area of the FET. Also, by having the reference and sensing electrodes on different surfaces of the substrate, it is possible to more easily manufacture the device described herein. However, in other applications, it may be desirable to place the reference electrode on another surface of the substrate. In any event, the reference electrode 49 may be electrically connected to an area adjacent to the source of the FET through highly doped region 38.

In the preferred embodiment, it is envisioned that the area of the substrate 34 on which the reference electrode is to be deposited is prepared as discussed below to provide efficient electrical connection between the substrate and the reference electrode. In the preferred embodiment, it is desired that the surface of the substrate on which the reference electrode 49 is to be deposited be highly doped in the same polarity as the polarity of the doped substrate. Therefore, a layer 50 is illustrated as an n+ region on the underside of the substrate. On top of the n+ layer is a layer 52 of chromium or aluminum for electrical contact with the substrate and for adhesion of subsequent layers. Over the layer of chromium or aluminum 52 a layer of silver/silver chloride with potassium chloride 54 is provided to form a stable, electrochemically well-defined reference electrode. A layer of cellulose acetate butyrate may be used as the reference membrane 49 in the preferred embodiment. However, other materials, such as any inert non-ion sensitive polymeric materials, may be used depending on the properties to be monitored to provide a reference level of the chemicals in the blood stream.

Figure 4:
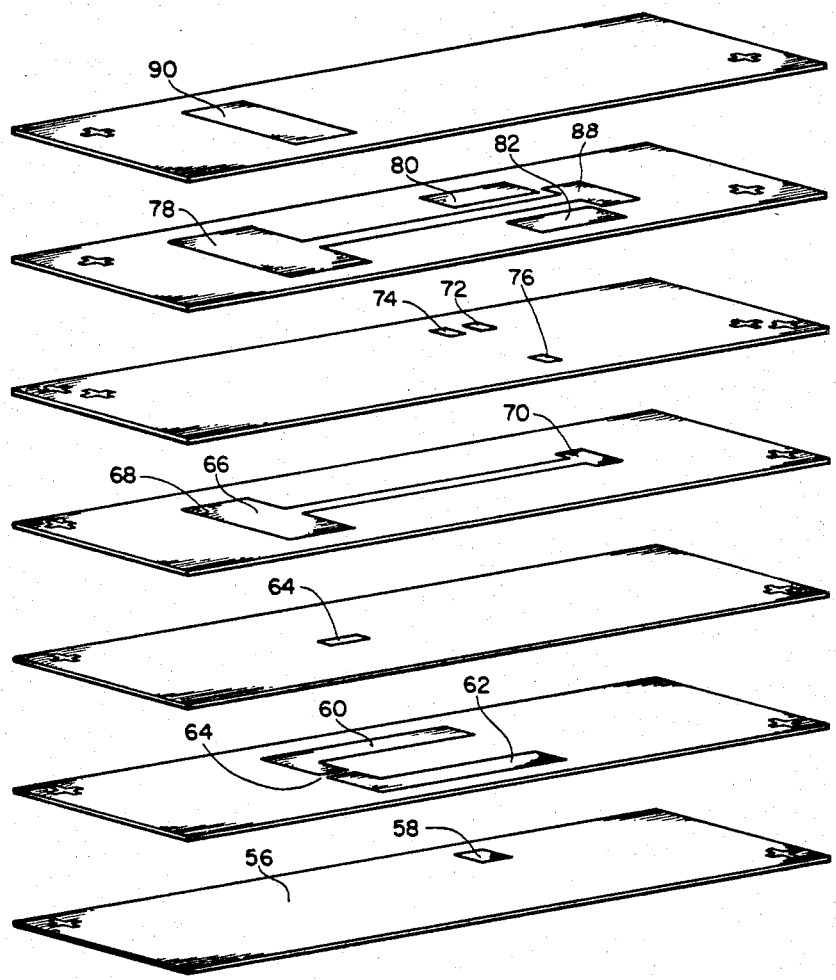
FIG. 4 is an exploded view of multiple layers of the present invention in its currently preferred embodiment.

FIG. 4 is provided to further illustrate the preferred embodiment of the subject development. FIG. 4 illustrates the manufacture of the working area of the FET. This can be seen in the figure, a substrate 56 is first provided with a highly doped n+ region 58 when the substrate is an n-doped substrate. In the preferred embodiment, the next step of manufacture is to provide source and drain 60, 62 respectively, diffusion regions. In this embodiment, since the substrate is an n-doped substrate, the source and drain regions are p-doped regions. As one can see from the figure, the n+ region 58 is very near the source 60. In the preferred embodiment, the source and drain regions are elongated L-shaped regions with a narrow gap in between which forms the gate region 64. In the preferred embodiment, it is desired to provide a "clear" area in the gate region to produce a good, clean oxide in the gate region. The purpose of the oxide is to keep the number of interface charges and interface states low and to keep the gate area free of sodium ions.

The next step in the manufacture of the preferred embodiment of the present invention is to provide a layer of polysilicon 66 which extends through the gate region 64. The layer of polysilicon extends parallel to the longer leg of the L-shaped source and drain diffusion areas beyond the lengths of the source and drain diffusion areas to provide a first region 68 away from the gate region 64. The first region 68 will have a chemically sensitive membrane deposited thereon at a later point in manufacture. The layer of polysilicon 66 is formed so as to provide a second separated region 70 extending beyond the opposite ends of the length of the source and drain diffusions as the first isolated region 68. The second region is used to test the FET to see if it is electrically acceptable, i.e. to test its source-to-drain current at zero bias.

After the polysilicon layer 66 has been deposited and shaped, in the preferred embodiment it is desired to provide contact openings 72, 74, 76 in the oxide layer over the n+ region 58 and at the uppermost portion of the longer leg of the L-shaped source and drain diffusion regions. Over contact openings 72, 74, and 76 and over the polysilicon layer 66, a layer of aluminum 78, 80, 82 is provided to form low-resistive contacts to the source, drain, gate, and n+ regions and to provide a material to which wire bonding can be performed. It is important to note that the aluminum layer is deposited everywhere the polysilicon layer 66 was deposited. In addition, the aluminum layer 78 is deposited across the drain region and across contact openings 72, 74, and 76. A diagnostic contact pad 88 is also provided for parametric testing of the device. Contact pad 90 of silver/silver chloride/potassium chloride is provided to produce a good electrochemical electrode for ion sensing.

After the chemically sensitive layer has been deposited on the entire substrate and the reference membrane has been deposited, the entire area is completely encapsulated in an encapsulant. The encapsulant does not cover the two contact pads 80 and 82, the reference membrane area, and the chemically sensitive membrane area.

Figure 5:
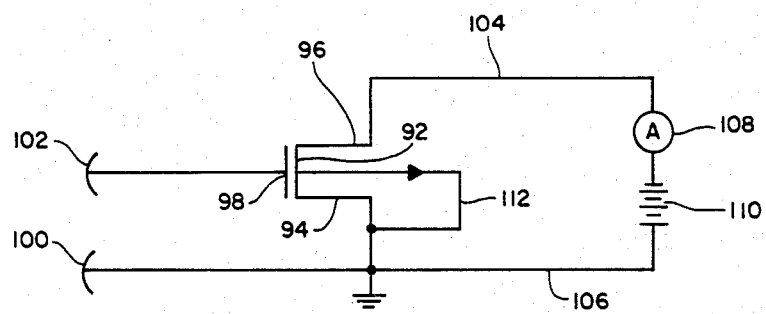
FIG. 5 is a simplified electrical circuit illustrating the relationship between various components of the present invention.

FIG. 5 is an illustration of an electrical circuit diagram representing the way in which the present invention operates. The FET 92 includes a source 94, a drain 96, and a gate 98. Reference electrode 100 is electrically attached to the source 94 while sensing electrode 102 is electrically connected to the gate 98 of the FET 92. Electrical leads 104 and 106 connect the source and drain of the FET to a current meter 108 and a battery 110 in series. As can be seen from the figure, the substrate is represented by line 112 which is electrically connected to the source 94.

The present invention envisions an alternative embodiment in which the sensing and reference electrodes may be on the same side of the substrate. Another embodiment envisions that a plurality of FETs or bipolar transistors may be used to amplify the signal from the input impedance transformer. The plurality of transistors may be integrated on the same substrate.

Although the invention has been described and illustrated in detail, it is to be clearly understood that the same is by way of illustration and example only and is not to be taken by way of limitation, the spirit and scope of this invention being limited only by the terms of the appended claims.

We claim:

1. A chemically sensitive device for monitoring chemical properties, comprising:
    a semiconductor substrate formed from material being slightly doped toward a first polarity;
    a depletion-mode field-effect transistor on said substrate, said field-effect transistor having source and drain regions oppositely doped with respect to said substrate with a lightly doped gate region thereinbetween also oppositely doped with respect to said substrate;
    a first highly doped region on said substrate of the same polarity of said substrate in electrical contact with said source of said field-effect transistor;
    a reference electrode having a reference membrane on said substrate, said reference electrode providing a first potential to said source through said first highly doped region;
    a chemically sensitive electrode having a chemically sensitive membrane on said substrate, said chemically sensitive membrane having an increased sensitivity to said chemical property to be monitored relative to said reference membrane, said chemically sensitive electrode being electrically connected to said gate to provide a chemically dependent potential to said gate; and
    means for monitoring the current between said source and said drain.

2. A chemically sensitive device for monitoring chemical properties as recited in claim 1, wherein said reference membrane is located on a side of said substrate different from a side of said substrate on which said source and drain regions are located.

3. A chemically sensitive device for monitoring chemical properties as recited in claim 1, wherein said chemically sensitive membrane is located on said substrate at a location geometrically remote but electrically connected to said gate.

4. A device as recited in claim 1, wherein said means for monitoring said current between said source and drain includes first and second electrical leads on said source and drain respectively to measure a current which is functionally related to the chemical property to be monitored.

5. A chemically sensitive device for monitoring chemical properties as recited in claim 1, further comprising: a thin-film layer of aluminum between said first highly doped region and said source to provide electrical connection between said first highly doped region and said source.

6. A chemically sensitive device for monitoring chemical properties, comprising:
    an impedance transformer including a depletion-mode field-effect transistor having a substrate, and source, drain, and gate regions on said substrate;
    reference electrode means for monitoring a general chemical composition, said reference electrode being supported by such substrate remote from, but internally electrically connected through said substrate to, said source;
    chemical sensing means for sensing a particular chemical to be monitored, said chemical sensing means being supported by said substrate remote from, but electrically connected to, said gate; and
    detection means for producing an output signal indicating the difference between the electrical potentials of said reference electrode means and said chemical sensing means, said detection means including a first electrical lead connected to said source and said second electrical lead connected to said drain.

7. A chemically sensitive device as recited in claim 6, wherein said substrate is lightly doped to have a first polarity and said source and drain are lightly doped to have a second polarity opposite said first polarity, and said impedance transformer further includes a first highly doped region near said source said first highly doped region having said first polarity, said highly doped region providing for an electrical connection between said reference electrode means and said substrate near said source.

8. A chemically sensitive device as recited in claim 7, wherein said impedance transformer includes a thin film of electrically conductive material between said first highly doped region and said source.

* * * * *